United States Patent [19]

Seckinger

[11] Patent Number: 4,579,585
[45] Date of Patent: Apr. 1, 1986

[54] N'-[4-(1-FLUOROMETHYL-ETHYL)-PHENYL]-UREA DERIVATIVES

[75] Inventor: Karl Seckinger, Riegel, Fed. Rep. of Germany

[73] Assignee: Sandoz Ltd., Basel, Switzerland

[21] Appl. No.: 707,668

[22] Filed: Mar. 4, 1985

Related U.S. Application Data

[63] Continuation of Ser. No. 457,004, Jan. 10, 1983, abandoned.

[30] Foreign Application Priority Data

Jan. 15, 1982 [GB] United Kingdom ............ 8201108

[51] Int. Cl.$^4$ .................. A01N 47/30; C07C 127/22; C07C 127/19
[52] U.S. Cl. ..................................... 71/120; 564/45; 564/52; 564/53; 564/54; 560/314
[58] Field of Search ............ 564/45, 52, 53, 54; 71/120; 260/453 RW

[56] References Cited

U.S. PATENT DOCUMENTS

| | | | |
|---|---|---|---|
| 3,734,961 | 5/1973 | Englehart ................. | 564/52 X |
| 4,093,742 | 6/1978 | Neustadt .................. | 564/53 X |
| 4,111,683 | 9/1978 | Singer ..................... | 564/53 X |
| 4,248,621 | 2/1981 | Seckinger et al. ......... | 71/120 |
| 4,406,691 | 9/1983 | Szczepanski ............. | 564/53 X |

FOREIGN PATENT DOCUMENTS

| | | |
|---|---|---|
| 1078407 | 5/1980 | Canada . |
| 0073727 | 3/1983 | European Pat. Off. ............. 71/120 |
| 2260861 | 6/1974 | Fed. Rep. of Germany . |
| 2501729 | 7/1976 | Fed. Rep. of Germany ........ 564/53 |
| 1407586 | 9/1975 | United Kingdom . |

OTHER PUBLICATIONS

Farm Chemicals Handbook, 1976, p. D19.

Primary Examiner—Thomas A. Waltz
Attorney, Agent, or Firm—Gerald D. Sharkin; Richard E. Vila

[57] ABSTRACT

The invention provides novel phenylurea of formula I

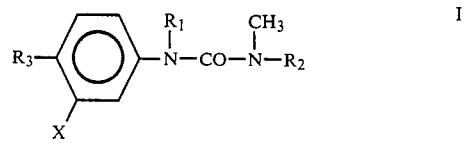

wherein
R$_1$ is H or CHO,
R$_2$ is H, CH$_3$ or OCH$_3$
R$_3$ is a group G$_1$ of the formula

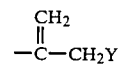

or a group G$_2$ of the formula CH(CH$_3$)CH$_2$Y in which Y is halogen selected from Cl or F or is CH$_3$O and
X is H or halogen selected from Cl or Br, the use of these novel compounds as herbicides, compositions for facilitating such use and the preparation of the novel phenylurea.

12 Claims, No Drawings

N'-[4-(1-FLUOROMETHYL-ETHYL)PHENYL]-UREA DERIVATIVES

This is a continuation of application Ser. No. 457,004 filed Jan. 10, 1983, now abandoned.

The present invention relates to phenylurea, their use as herbicides, compositions for facilitating such use and the preparation of these phenylureas.

The invention provides compounds of formula I

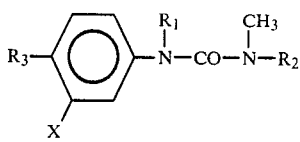

wherein
$R_1$ is H or CHO,
$R_2$ is H, $CH_3$ or $OCH_3$
$R_3$ is a group $G_1$ of the formula

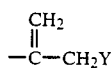

or a group $G_2$ of the formula $CH(CH_3)CH_2Y$ in which Y is halogen selected from Cl or F or is $CH_3O$ and
X is H or halogen selected from Cl or Br.

The present invention also provides processes for producing phenylurea of the invention comprising (a) reacting under urea condensation reaction conditions
a compound of formula II

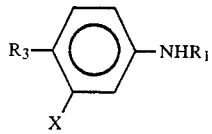

wherein $R_1$, $R_3$ and X are as defined above with a compound formula III

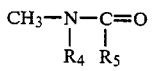

wherein either
$R_4$ is $CH_3$ or $OCH_3$ and $R_5$ is halogen
or
$R_4$ and $R_5$ together form a single bond,
or (b) obtaining a compound of formula Ia

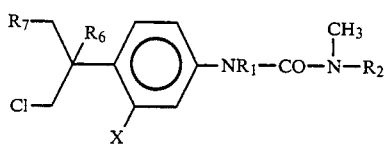

wherein
$R_1$, $R_2$ and X are as defined above and either $R_6$ and $R_7$ are both H
or
$R_6$ and $R_7$ together form a single bond
by substituting in a compound of formula IV

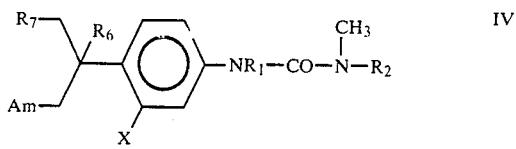

wherein
$R_1$, $R_2$, $R_6$, $R_7$ and X are as defined above,
Am is morpholine or a di($C_{1-4}$alkyl)N group the Am by Cl
or (c) obtaining a compound of formula Ib

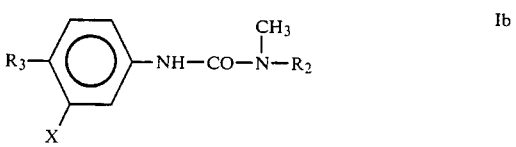

wherein $R_2$, $R_3$ and X are as defined above by reacting under the conditions of an urea addition reaction a compound of formula V

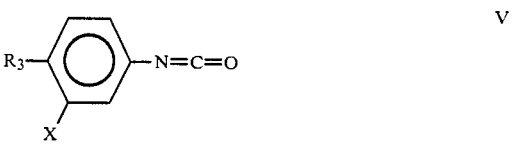

wherein $R_3$ and X are as defined above with an amine of formula VI

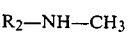

wherein $R_2$ is as defined above.

The reaction of a compound of formula II with a compound of formula III, hereinafter designated process (a), may be effected in an aprotic organic solvent which is inert under the reaction conditions at a reaction temperature of 0°–25° C., e.g. at room temperature.

Where the compound of formula III is a carbamoyl-halide, the organic solvent is preferably a polar solvent such as dimethylformamide, where the compound of formula III is an isocyanate, reaction (a) is advantageously effected in a polar solvent, e.g. an ether such as diethylether.

The reaction with carbamoyl halide is preferably effected in the presence of an acid acceptor, e.g. an amine such as triethylamine. Where $R_5$ is halogen, this is selected from Cl or Br and is preferably Cl.

The reaction with methylisocyanate is advantageously effected in the presence of catalytic amounts of dibutyl tin diacetate.

Under the above reaction conditions, reaction (a) is in general complete after 10 to 50 hours.

A suitable significance of Am in the compounds of formula IV is dimethylamino. The substitution of the Am group in the compounds of formula IV by Cl may, for example, be effected by reacting a compound of formula IV with phosgene or a chloroformic acid ester, e.g. the phenyl ester in an organic solvent which is inert under the reaction conditions, e.g. a halogenated hydrocarbon such as $CH_2Cl_2$. The reaction may be effected at room temperature.

The preparation of the compounds of formula Ib according to process (c) may be effected under the reaction conditions indicated for the reaction of methyl isocyanate with a compound of formula II according to process (a).

The compounds of formula I may be recovered from the reaction mixture in which it is formed by working up by established procedures.

The starting materials of the formula II, IV and V are novel.

The anilines of formula II may be obtained by reduction of the corresponding nitrobenzenes of formula VII

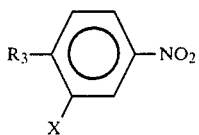

VII wherein $R_3$ and X are as defined above, followed, if desired, by N-formylation of the obtained aniline, e.g. with the aid of HCOOH.

The reduction of compounds of formula VIIa

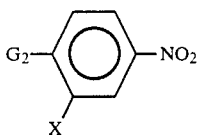

VIIa wherein $G_2$ and X are as defined above, may for example be effected with the aid of $H_2$/Pd or $H_2$/Raney Nickel. Where the preparation of compounds of formula II is intended wherein $R_3$ is a group $G_1$, as defined above, the reduction of the corresponding $NO_2$ compounds of formula VII is effected selectively, e.g. in accordance with Béchamp with the aid of $FeCl_3$/HCl.

An example of a suitable reaction scheme for the preparation of compounds of formula VII is as follows:

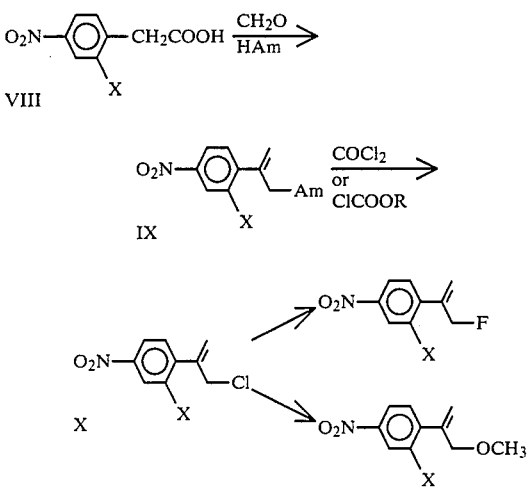

The conversion of the compounds of the formula VIII to the compounds of formula IX is effected under the conditions of a Mannich reaction. Am is particularly morpholino or dimethylamino. Nucleophilic substitution of the allylic Cl in the formula X by F, e.g. with KF or by $OCH_3$, e.g. with $NaOCH_3$, yields the compounds of formula XI and XII resp.

The compounds of formula VIIa wherein X is hydrogen may be converted in the corresponding compounds wherein X is Br with the aid of $K_2BrO_3$ (see Example 21 hereinafter).

The compounds of the formula X, XI and XII may be converted to the corresponding compounds of formula VIIa by selective hydrogenation of the allylic double bond e.g. with hydroxylamine-O-sulphonic acid or with tristriphenylphosphine rhodiumchloride (the latter being preferred when Y is Cl).

Compounds of formula V may be obtained by reaction of compounds of formula II (wherein $R_1$ is hydrogen) with phosgene.

Insofar as the production of starting material is not described herein, these compounds are known, or may be produced and purified in accordance with known processes or in a manner analogous to processes described herein or to known processes.

The compounds of the invention are useful as herbicides, whereby herbicide as used herein means a compound which controls or modifies the growth of plants. The term plant as used herein embraces germinant seeds, emerging seedlings and established vegetation including underground portions.

The useful herbicidal activity of the compounds of the invention is indicated by i.a. the damage caused to both monocotyledoneous and dicotyledoneous weeds such as *Lepidium sativum, Avena sativa, Agrostis alba* and *Lolium perenne* in tests by test dosages equivalent to an application rate of from 1.4 to 5.6 kg/ha after pre- or post-emergence application. In view of their herbicidal effect the compounds of the invention are indicated for use in combatting dicotyledoneous and grassy weeds, as confirmed by further evaluation with representative compounds with test dosages equivalent to an application rate of from 0.2 to 5.0 kg active ingredient, e.g. test dosages equivalent to a rate of 0.2, 1.0 and 5.0 kg active ingredient/ha, in dicotyledoneous weeds such as *Amaranthus retroflexus, Capsella bursapastoris, Chenopodium alba, Stellaria media, Senecio vulgaris, Galium aparine,* Portulaca spp., *Ipomoea purpurea, Sesbania exaltata, Xanthium pensylvanicum, Sida spinosa, Anoda cristata, Solanum nigra* and Abutilon spp. and grassy weeds such as *Agropyron repens, Agrostis alba, Alopecurus myosuroides, Apera spica venti, Avena fatua, Echinochloa crusgalli, Lolium perenne, Sorghum halepense, Digitaria sanguinalis, Setaria italica, Setaria lutescens, Sorghum bicolor, Bromus tectorum, Brachiara platyphylla, Leptochloa dubia* and *Panicum* spp.

The compounds of the invention are relatively less toxic towards crops, e.g. grassy crops such as a small grain (wheat, barley, upland rice, paddy rice) or corn (maize) or against broad leaved crops such as soybean, cotton, potato than towards weeds. The compounds of the invention are therefore also indicated for use as selective herbicides in a crop locus.

Said selective herbicidal activity of the compounds of the invention is, for example, noted after pre-emergence application in a crop locus including a small grain crop, such as wheat or rice, potato, soybean and cotton. The selective herbicidal effect of the compounds of the invention is also noted after post-emergence application to a crop locus including i.a. corn, potato, soybean, cotton and small grain crops such as wheat and rice. This post-emergence selective herbicidal activity is particularly effective in corn, wheat and soybean.

Particularly advantageous herbicidal properties are observed with compounds of formula I having one or more of the following features:

$R_1$ is H
$R_3$ is $CH(CH_3)CH_2Y$
Y is F or Cl.

Examples of compounds having valuable herbicidal activity are those of the Examples 4.3, 6, 7.2, 7.3, 7.4, 7.5 and 7.6 hereinafter. Compared to known standard urea compounds such as N'-[4-(1-methylethyl)phenyl]-N,N-dimethylurea, they show improved activity against broad leaf weeds while maintaining the excellent herbicidal activity against annual grassy weeds, an improved activity against Galium and/or improved selectivity in soya. The compounds of Example 4.3 is, in view of its excellent activity against dicotylodoneous weeds particularly indicated for use as a selective herbicide in wheat, corn (mais), rice, soybean and potato. The compound of Example 6 allows a good control of annual grasses and dicotyledoneous weeds at pre- and post-emergence application (at rates between 1 to 2 kg active ingredient-/ha), it shows good selectivities in corn, wheat and potato, whereby pre-em applications are slightly preferred over post-em applications.

The compounds of Example 7.2 shows pre-em and post-em selectivity in soya; with application rates of 5 kg active ingredient/ha no significant damage to soya, and excellent control of grassy and dicotyledoneous weeds is observed. The compound of Example 7.3 has excellent dicotyledoneous, including Galium activity in wheat, corn, soybean and potatoes, both after pre- and post-em application. The potatoes, both after pre- and post-em application. The compound of Example 7.4 is particularly indicated for post-em application: good selective herbicidal activity (including Galium control) is observed in wheat and corn with application rates of 1 kg/ha. The compound of Example 7.5 is pre-em and especially post-em more active against dicotyledoneous weeds (including Galium) than the standard indicated hereinbefore, and shows good selectivity in wheat, corn, soybean and potato. The compound of Example 7.6 is post-em more active against dicotyledoneous weeds than the standard indicated hereinbefore and shows good selectivity in corn, wheat and soybean.

The present invention therefore also provides a method of combatting weeds in a locus, preferably in a crop locus as mentioned above, which comprises applying to the locus a herbicidally effective amount of a compound of the invention.

For general herbicidal as well as for selective herbicidal use of compounds of the invention, the amount to be applied to attain the desired effect will vary depending on the particular crop if employed for selective use and other standard variables such as the compound employed, mode of application, conditions of treatment and the like. The appropriate application rates can be determined by routine procedures by those skilled in the art, or by comparing the activity of the compounds of the invention with standards for which the application rate is known, e.g. in greenhouse tests. However, in general, satisfactory results are usually obtained when the compound is applied at a rate in the range of from about 0.1 to 5 kg/ha, preferably from about 0.5 to 2 kg/ha, e.g. 1.0 kg/ha, the application being repeated as necessary.

The compounds of the invention may be and preferably are employed as herbicidal compositions in association with herbicidally acceptable diluent(s). Suitable formulations contain 0.01% to 99% by weight of active ingredient, from 0 to 20% herbicidally acceptable surfactant and 1 to 99.99% solid or liquid diluent(s). Higher ratios of surfactant to active ingredient are sometimes desirable and are achieved by incorporation into the formulation or by tank mixing. Application forms of composition generally contain between 0.01 and 25% by weight of active ingredient. Lower or higher levels of active ingredient can, of course, be present depending on the intended use and the physical properties of the compound. Concentrate forms of composition intended to be diluted before use generally contain between 2 and 90%, preferably between 10 and 80% by weight of active ingredient.

Useful formulations of the compounds of the invention include dusts, granules, pellets, suspension concentrates, wettable powders, emulsifiable concentrates and the like. They are obtained by conventional manner, e.g. by mixing the compounds of the invention with the diluent(s). More specifically liquid compositions are obtained by mixing the ingredients, fine solid compositions by blending and grinding, suspension concentrates by wet milling and granules by spraying a solution of the active material in a suitable solvent onto preformed granular carriers or by coating of granular carriers such as sand with finely divided solid active ingredients or by agglomeration techniques (e.g. in a fluidized bed). Pellets are obtained by e.g. compacting powder mixtures containing the active ingredient.

Alternatively, the compounds of the invention may be used in microencapsulated form.

Herbicidally acceptable additives may be employed in the herbicidal compositions to improve the performance of the active ingredient and to reduce foaming, caking and corrosion.

Surfactant as used herein means a herbicidally acceptable material which imparts emulsifiability, spreading, wetting, dispersibility or other surface-modifying properties. Examples of surfactants are sodium lignin sulphonate and lauryl sulphate.

Diluents as used herein mean a liquid or solid herbicidally acceptable material used to dilute a concentrated material to a usable or desirable strength. For dusts or granules it can be e.g. talc, kaolin or diatomaceous earth, for liquid concentrate forms for example a hydrocarbon such as xylene or an alcohol such as isopropanol, and for liquid application forms i.a. water or diesel oil.

The compositions of this invention can also comprise other compounds having biological activity, e.g. compounds having similar or complementary herbicidal activity or compounds having antidotal, fungicidal or insecticidal activity.

Specific Examples of herbicidal compositions will now be described.

It will be appreciated that the examples are non-limitative; the compounds of Examples 1, 2, 3, 4.1, 4.2, 4.3 and 5 hereinafter are, for example, also obtained analogous to process (c), the compounds of Example 5, 6 and 7.1 to 7.4 are also obtained according to process (a), etc.

EXAMPLE A

Wettable Powder

25 Parts of a compound of the invention, e.g. the compound of Example 1 hereinafter given are mixed and milled with 25 parts of synthetic fine silica, 2 parts of sodium lauryl sulphate, 3 parts of sodium ligninsulphonate and 45 parts of finely divided kaolin until the mean particle size is about 5 micron. The resulting wettable powder is diluted with water before use to a spray liquor with the desired concentration.

EXAMPLE B

Emulsion Concentrate

25 Parts of a compound of the invention, e.g. the compound of Example 1 hereinafter given, 10 parts of xylene, 15 parts of isophorone and 40 parts of dimethylformamide and 10 parts of emulsifier (e.g. ATLOX 4851 B a blend of Ca alkylarylsulphonate and a polyethoxylated triglyceride of Atlas Chenie GmbH) are thoroughly mixed until a homogeneous solution is obtained. The resulting emulsion concentrate is diluted with water before use.

EXAMPLE C

Granules

5 Kg of a compound of the invention, e.g. the compound of Example 1 hereinafter given, are mixed with 0.2 kg of synthetic fine silica and finely milled. The resulting powder is added in a suitable mixture to 94 kg of quartz sand in granular form (particle size 24/48 mesh/inch) previously moistened with 1.5 kg of a 50% polyvinylacetate emulsion, until a uniform coating is obtained. The coated granules are dried by a stream of hot air.

The invention is further illustrated by the following examples wherein temperatures are in °C.

FINAL COMPOUNDS

EXAMPLE 1

N'-[4-(1-Methoxymethyl-ethenyl)phenyl]-N,N-dimethyl urea 10.2 g (0.062 Mol) 4-(1-methoxymethyl-ethenyl)-aniline, 6.8 g (0.063 Mol) dimethylcarbamoyl chloride and 6.4 g (0.063 Mol) triethylamine are dissolved in 40 ml dimethylformamide and the reaction solution stirred for 50 hours at room temperature.

The reaction solution is poured into 2000 ml $H_2O$ and extracted with $CH_2Cl_2$. The organic phase is dried ($Na_2SO_4$) and evaporated in vacuo. The residual viscous oil is chromatographed on silica gel with diethylether/n-hexane 2:1 as an eluant to give the title compound in the form of colourless crystals, m.p. 96°–97°.

EXAMPLE 2

Following the procedure of Example 1, but employing the appropriate compound of formula II and carbamoyl chloride of formula III, are obtained 2.1 N'-[4-(1-fluoromethyl-ethenyl)phenyl]-N,N-dimethyl-urea m.p. 144°–145°.

EXAMPLE 3

N-[4-(1-methoxymethyl-ethenyl)phenyl]-N-methyl urea

To a solution of 8.2 g (0.05 Mol) 4-(1-methoxymethyl-ethenyl)aniline in 200 ml absolute diethylether are added, at ambient temperature, 4 ml (0.067 Mol) methylisocyanate. The resulting reaction solution is, after the addition of 0.3 g dibutyl tin diacetate, kept at room temperature for 20 hours.

The reaction mixture is then cooled to 0° and the precipitated crystals filtered off, to give the analytically pure title compound m.p. 84°–85°.

EXAMPLE 4

Following the procedure of Example 3, but employing appropriate compounds of formula II and methylisocyanate, are obtained 4.1 N'-[4-(1-fluoromethyl-ethenyl)phenyl]-N-methyl urea m.p. 164°.

4.2 N'-[4-(1-methoxymethyl-ethyl)phenyl]-N-methyl urea, m.p. 131°–132°

4.3 N'[4-(1-fluoromethyl-ethyl)phenyl]-N-methyl urea, m.p. 117°

4.4 N'-[4-(1-fluoromethyl-ethyl)phenyl]-N'-formyl-N-methyl urea, m.p. 139°–140°.

EXAMPLE 5

N'-[4(1-chloromethyl-ethenyl)phenyl]-N-methyl urea

To a solution of 13.85 g (0.06 Mol) N'-[4(1-dimethylaminomethyl-ethenyl)phenyl]-N-methyl urea in 180 ml absolute $CH_2Cl_2$ are added dropwise, at 20°–30°, within 20 minutes, 9.4 g (0.06 Mol) chloroformic acid phenyl ester in 50 ml absolute $CH_2Cl_2$.

When the addition is complete, the reaction mixture is stirred 4 hours at room temperature and then evaporated to give a light brown viscous residue that is chromatographed on a silica gel column. Elution with acetic acid ethyl ester/$CH_3OH$ 4:1 afforded the title compound in the form of colourless crystals, m.p. 133°–135°.

EXAMPLE 6

N'-[4-(1-Fluoromethyl-ethyl)phenyl]-N,N-dimethyl urea (process c))

To 46.6 g (0.47 Mol) phosgene in 350 ml absolute acetic acid ethyl ester are added dropwise, with stirring, at 0°–5° a solution of 19.9 g (0.13 Mol) 4-(1-fluoromethyl-ethyl)aniline in 100 ml absolute acetic acid ethyl ester. When the addition is complete the reaction mixture is stirred for 2 hours at room temperature and then concentrated by evaporation in vacuo.

The thus obtained crude 4-(1-fluoromethyl-ethyl)-phenylisocyanate is dissolved in 250 ml absolute diethylether and filtered. To the filtrate are added dropwise at 10° (ice water cooling), after the addition of 0.3 g dibutyl tin diacetate, a solution of 12.2 g (0.27 Mol) dimethylamine in 200 ml absolute diethylether. The formed crystalline precipitate is filtered off and washed with diethylether to yield the analytically pure title compound m.p. 145°–146° (Upon recrystallization from acetic acid ethyl ester, the title compound had a m.p. of 158°–9°.

EXAMPLE 7

Following the procedure of Example 6 but employing appropriate starting compounds of formula V the following compound of formula Ib is obtained 7.1 N'-[4-(1-methoxymethyl-ethyl)phenyl]-N,N-dimethyl urea m.p. 106°–107°.

7.2 N'-[4-(1-chloromethyl-ethyl)phenyl]-N,N-dimethyl urea, m.p. 139°–141°

7.3 N'-[3-bromo-4-(1-fluoromethyl-ethyl)phenyl]-N,N-dimethyl urea, m.p. 144°–146°

7.4 N'-[4-(1-fluoromethyl-ethyl)phenyl]-N-methoxy-N-methyl urea, m.p. 78°–80°

7.5 N'-[3-chloro-4-(1-fluoromethyl-ethyl)phenyl]-N,N-dimethyl urea, m.p. 141°–142°

7.6 N'-[3-chloro-4-(1-chloromethyl-ethyl)phenyl]-N,N-dimethyl urea, m.p. 128°

INTERMEDIATES

EXAMPLE 8

1-[2-(p-Nitrophenyl)allyl]morpholine

To 567 g (3.13 Mol) p-nitrophenylacetic acid and 400 ml $H_2O$ are added, dropwise, at 45°–55° within 20 minutes, 555 ml (6.35 Mol) morpholine. The mixture is stirred for 1 hour at 45°. Thereto are added, also at 45°, within 30 minutes, 635 ml (7.4 Mol) 30% formaldehyde solution.

The reaction solution is stirred at 45° for 20 hours and then cooled. 4000 ml $H_2O$ are added and the aqueous solution extracted with $CH_2Cl_2$. The $CH_2Cl_2$ phase is washed with water, dried over $Na_2SO_4$ and evaporated to dryness. The viscous residue stiffens to a crystalline mass, m.p. 62–63°.

EXAMPLE 9

N,N-Dimethyl-β-methylen-4-nitro-phenylethane amine

One proceeds analogous to Example 8, using dimethylamine instead of morpholine and obtains the title compound, b.p. 60°/1.5 Torr.

EXAMPLE 10

4-(1-Chloromethyl-ethenyl)-nitrobenzene

To 445 g (1.79 Mol) 1-[2-(p-nitrophenyl)allyl]-morpholine in 2500 ml absolute $CH_2Cl_2$ is added, dropwise, while stirring, within 45 minutes, at room temperature a solution of 180 g (1.82 Mol) phosgene in 1100 ml absolute $CH_2Cl_2$.

When the addition is complete the reaction mixture is stirred a further 2 hours, kept over night at room temperature and then evaporated in vacuo. The side product, 4-morpholinecarbonyl chloride, is distilled off under high vacuum (93°/1.5 Torr) and the distillation residue chromatographed on silica gel. The title compound is obtained with $CH_2Cl_2$ as eluant, m.p. 43°–45°.

EXAMPLE 11

4(1-Fluoromethyl-ethenyl)-nitrobenzene

Under a $N_2$ blanket is stirred a mixture of 296.5 g (1.5 Mol) 4(1-chloromethyl-ethenyl)-nitrobenzene, 430 g (7.4 Mol) KF, 78 g (0.15 Mol) hexadecyltributylphosphonimine bromide and 800 ml $H_2O$, during 5 hours at 110°–112°.

Thereto are added 3000 ml ice water and the mixture extracted with 500 ml $CH_2Cl$. The $CH_2Cl_2$ extract is washed with five 2000 ml portions of water, dried over $Na_2SO_4$ and evaporated in vacuo.

The residue is chromatographed on 2800 g silica gel with $CH_2Cl_2/CCl_4$ 2:1 as eluant to give the title compound in the form of colourless crystals, m.p. 30°–31°.

EXAMPLE 12

4(1-Fluoromethyl-ethyl)-nitrobenzene

To a solution of 17.5 g (0.1 Mol) 4(1-fluoromethylethenyl)-nitrobenzene in 400 ml $CH_3OH$ are added 100 g (0.8 Mol) 90% hydroxylamine-O-sulphonic acid and 67.2 g (0.41 Mol) hydroxylamine sulphate. The reaction mixture is then rendered alkaline (pH 8) at 15°–20° cooling with ice water) with 20% aqueous NaOH. After the addition of a further 500 ml portion of $CH_3OH$ the reaction mixture is stirred at room temperature for 24 hours, and then filtered. The filtrate is evaporated in vacuo. The residue is dissolved in $CH_2Cl_2$, this solution washed with $H_2O$, dried over $Na_2SO_4$ and evaporated. The light yellow, chromatographically (this layer) pure liquid (Rf=0.5; $CHCl_3/CCl_4$ 1:1 on silica gel) is vaccum distilled, to give the title compound, b.p. 103°–104°/0.1 Torr.

EXAMPLE 13

4(1-Fluoromethyl-ethyl)-aniline 10.3 g (0.057 Mol) 4(1-fluoromethyl-ethyl)-nitrobenzene are dissolved in 250 ml absolute $CH_3OH$ and hydrogenated at room temperature and atmospheric pressure in the presence of 0.61 g 10% Pd/C.

The reaction stops after the calculated amount of $H_2$ has been taken up. The catalyst is filtered off and the filtrate evaporated. The resulting chromatographically (thin layer) pure, colourless liquid (Rf=0.2 on silica gel, with $CHCl_3$) vacuum distilled, to give the title compound, b.p. 86°–88°/0.3 Torr.

EXAMPLE 14

4(1-Methoxymethyl-ethenyl)-nitrobenzene

To a $CH_3ONa$-solution from 6.9 g (0.3 gramatom) Na and 600 ml absolute $CH_3OH$ are added 59.3 g (0.3 Mol) 4(1-chloromethyl-ethenyl)-nitrobenzene, the reaction mixture heated under reflux for 2 hours and then evaporated to dryness. The residue is digested with diethylether, the ethereal solution filtered and the filtrate concentrated by evaporation. The residue is then chromatographed on silica gel (eluant n-hexane/diethylether 1:1) to give the title compound in analytically pure form (Rf=0.37 on silica gel with $CHCl_3$).

EXAMPLE 15

4(1-Methoxymethyl-ethenyl)-aniline

To a well stirred mixture of 25.2 g (0.13 Mol) 4(1-methoxymethyl-ethenyl)-nitrobenzene and 72.2 g (1.4 gramatom) Fe powder in 105 g ethanol and 25 ml $H_2O$ are added 1.5 ml conc.HCl, dropwise, in such a way that the reaction temperature does not exceed 35°. After stirring for 7 hours at room temperature, the reaction mixture is filtered, and the filtrate concentrated by evaporation. Water is added to the residue and the mixture extracted with $CH_2Cl_2$. The combined $CH_2Cl_2$ extracts are washed with water, dried over $Na_2SO_4$ and the solvent evaporated off.

The resulting title compound is obtained as a light yellow liquid (Rf=0.4 on silica gel with diethylether).

EXAMPLE 16

4(1-Dimethylaminomethyl-ethenyl)-aniline

To a boiling mixture of 20.6 g (0.1 Mol) N,N-dimethyl-β-methylen-4-nitrophenylethane amine, 100 mg (0.0006 Mol) anhydrous $FeCl_3$, 2.2 g active coal and 50 ml $CH_3OH$ are added dropwise, within 30 minutes, 8 g (0.16 Mol) hydrazine-hydrate. After heating under reflux for 3 hours, the mixture is cooled, filtered and the filtrate concentrated by evaporation of the solvent.

The resulting dark brown viscous oil is dissolved in 30 ml diethylether, the ethereal solution filtered and the filtrate kept overnight at −20°. The resulting crystals are filtered off and washed with petrol ether/diethylether 10:1 to yield the analytically pure title compound, m.p. 71°–72°.

EXAMPLE 17

N'-[4(1-Dimethylaminomethyl-ethenyl)phenyl]-N-methyl urea

To 9.3 g (0.053 Mol) 4(1-dimethylaminomethylethenyl)-aniline in 220 ml absolute diethylether are added 5 ml (0.085 Mol) methylisocyanate and the reaction solution, after addition of 0.3 ml dibutyl tin diacetate, stirred over night, at room temperature. The crystals that precipitated after 18 hours are filtered off and washed with petrol ether to give the analytically pure title compound, m.p. 123°–124°.

EXAMPLE 18

4-(1-Chloromethyl-ethyl)aniline

The title compound (b.p. 93°–95°/0.01 Torr) is obtained analogous to the procedure of Example 13.

EXAMPLE 19

4(1-Chloromethyl-ethyl)-nitrobenzene

A solution of 51.3 g (0.26 Mol) of 4(1-chloromethylethenyl)-nitrobenzene and 10 g of tris(triphenylphosphine)-rhodium (I) chloride in 1000 ml of dry toluene is hydrogenated at ambient temperature and atmospheric pressure.

After 46 hours the homogeneous reaction solution is evaporated in vacuo. The isolation of the analytically pure title compound is performed by distilling the residue under diminished pressure. The fraction collected at 120°–122°/0.2 Torr solidifies soon to colourless crystals, having a m.p. of 51°–52°.

EXAMPLE 20

3-Chloro-4(1-chloromethyl-ethyl)-nitrobenzene 24 g (0.12 Mol) of 4(1-chloromethyl-ethyl)-nitrobenzene, 1 g of antimony trichloride, 50 mg of iodine and 16 mg of $PCl_3$ are gradually warmed to 60°. Through the resulting homogeneous syrup a current of dry chlorine is passed at such a rate that the temperature inside the flask does not rise above 70°. When little more than the theoretical amount of chlorine is absorbed (5.3 g/20 minutes) the brown reaction mixture is cooled to ambient temperature and then taken up in 125 ml of toluene. The toluene solution is washed with five 150 ml portions of water, dried ($Na_2SO_4$) and evaporaed in vacuo.

The brown oily residue is chromatographed on a silica gel column. Elution with $CCl_4$—$CHCl_3$ 10:1 affords the analytically pure title compound, having a m.p. of 45°–46°.

EXAMPLE 21

3-Bromo-4(1-fluoromethyl-ethyl)-nitrobenzene

To 80 ml of concentrated sulfuric acid, 80 ml of water and 18.3 g (0.1 Mol) of 4(fluoromethyl-ethyl)-nitrobenzene are added portionwise with stirring 18.3 g (0.11 Mol) potassium bromate at such a rate that the temperature does not exceed 35°.

When the addition is complete the reaction mixture is stirred at room temperature for a period of 18 hours resulting in the formation of an oil phase below the acid. The upper aqueous phase is extracted with $CH_2Cl_2$. The combined product layer and extract are washed twice with water, dried ($Na_2SO_4$) and evaporated in vacuo. The residual oil, after chromatography on silica gel (elution with hexane-diethylether 3:1) solidifies completely on chilling overnight at −20°; m.p. 20°–22°.

EXAMPLE 22

3-Chloro-4(-fluoromethyl-ethyl)-nitrobenzene

To a well stirred mixture of 45.1 g (0.24 Mol) of 4(1-fluoromethyl-ethyl)-nitrobenzene, 39.2 g (0.12 Mol) silver sulfate, 260 ml of conc. $H_2SO_4$ and 39 ml of water is added dropwise at ambient temperature the solution of 19.2 g (0.27 Mol) of chlorine in 400 ml of carbon tetrachloride.

When the addition is complete, stirring is continued for a further two hours. Then 1200 ml of water are added and the precipitated silver chloride filtered off through a sintered glass crucible.

The organic layer is separated, dried over anhydrous $Na_2SO_4$ and evaporated in vacuo. The isolation of the analytically pure title compound is performed by chromatography on silica gel using $CCl_4$ as eluant. A small portion of this material was subjected to ball tube distillation; b.p. 78°–80°/0.01 Torr.

EXAMPLE 23

3-Bromo-4(1-fluoromethyl-ethyl)-benzeneamine

A solution of 15.75 g (0.06 Mol) of 3-bromo-4(1-fluoromethyl-ethyl)-nitrobenzene in 200 ml of ethanol is hydrogenated for 45 hours at room temperature and atmospheric pressure in the presence of 3 g of Raney nickel.

When the reduction is complete the catalyst is filtered off and the filtrate evaporated in vacuo. The residual yellow liquid is chromatographed on silica gel. Elution with hexane-diethylether 3:2 yields the title compound as an analytically pure oil, Rf=0.22 (hexane-ether 1:1).

EXAMPLE 24

Analogous to the procedure of Example 23 are obtained:

EXAMPLE 24.1

3-Chloro-4(1-fluoromethyl-ethyl)benzeneamine;
Rf=0.21 (ether-hexane 2:1);
b.p. 88°–90°/0.01 Torr.

EXAMPLE 24.2

3-Chloro-4(1-chloromethyl-ethyl)hexaneamine;
Rf=0.22 (ether-hexane 1:1).

EXAMPLE 25

N[4(1-fluoromethyl-ethyl)phenyl]-formamide

A solution of 20 g (0.13 Mol) of 4(1-fluoromethylethyl)benzeneamine and 6 g (0.13 Mol) of 98% formic acid in 150 ml of dry toluene is boiled under reflux. When 2.5 ml of water have separated in the water trap, an additional 6 g of formic acid are added and refluxing is continued until no more water and formic acid separate.

The toluene solution is then washed with 100 ml of 5% sodium bicarbonate solution and dried over anhydrous $Na_2SO_4$. The crude title compound left on rotevaporation of the toluene is purified by distillation: b.p. 157°–160°/0.4 Torr, m.p. 42.44°.

TESTS

EXAMPLE 26

Weed Control—Pre-emergence treatment

Seed pots (7 cm diameter) are filled with a mixture of peat culture substrate and sand. The exposed surface of the past culture substrate and same mixture is sprayed with a test liquid of a test compound (e.g. formulated in accordance with Example B) and seeds of *Lepidium sativum, Agrostis alba, Avena sativa* and *Lolium perenne* are sown in each pot, whereby the *Avena sativa* and *Lolium perenne* seeds are, after sowing covered with a thin layer (0.5 cm) of peat culture substrate/sand mixture. The pots are kept for 21 days at room temperature with 14 to 17 hours light (daylight or its equivalent) per day.

Determination of the herbicidal effect of the particular herbicide is made after the 21 day period. The determination involves a visual evaluation of the degree and quality of damage to the various seed plants.

The compounds of formula I of the above Examples 1 to 7 are applied in the above manner at dosages equivalent to 1.4 and 5.6 kg of active agent/hectare.

Herbicidal activity is observed, that is to say, significant damage to the test plants is observed.

EXAMPLE 27

Weed control—Post-emergence treatment

A procedure similar to that employed in Example 26 is followed with the exception that the test compounds (herbicides) are applied when the plants are at the 2-4 leaf stage, the sowing of the plant seeds being staggered to ensure that the plants reach the 2-4 leaf stage at about the same time.

Again the compounds of the Examples 1 to 7 are applied in the above manner at dosages corresponding to 1.4 kg/ha and 5.6 kg/ha. The determination of the herbicidal effect is made 21 days after application of the test compounds and involves an analogous evaluation as described in Example 26. Herbicidal activity is observed.

EXAMPLE 28

Representative compounds of the invention are evaluated in the following pre-emergence test procedure.

Seed dishes measuring 30×40 cm are filled to a depth of 6 cm with a mixture of peat culture substrate and sand. The exposed surface of the peat culture substrate and sand mixture is sprayed with an aqueous test liquid (e.g. formulated in accordance with Example B) comprising a compound of the invention in a given concentration. The spray volume corresponds to 600 l aqueous test liquid/ha. The same test is repeated with various concentrations of test liquid, whereby the concentrations are selected in such a manner that the desired application rates are realized. Six species of seed are then sown in each dish. The number of seeds sown for each plant species depends on the seed germination potential and also the initial growth size of the particular seed plant. After sowing of the seeds, the treated surface is covered with a thin layer about 0.5 cm deep of the past culture and sand mixture.

The prepared seed dishes are kept for 28 days at a temperature of 20° to 24° C. and 14 to 17 hours light each day.

Determination of the herbicidal effect of the particular compound of the invention is made after the 28 day period. The determination involves a visual evaluation of the degree and quality of damage to the various seed plants. Particular advantageous herbicidal properties are i.a. observed with the compounds of the Examples 4.3, 6, 7.2, 7.3, 7.4, 7.5 and 7.6. Some of the results obtained with application rates corresponding to 0.2 kg, 1 kg and 5 kg active ingredient/hectare have been summarised herein before. (See also Table A hereinafter).

EXAMPLE 29

Post-emergence Treatment

A further evaluation of representative compounds of the formula I is effected in a post-emergence test procedure similar to that of the pre-emergence test described in Example 29, except that the herbicide test liquid is applied when the seeds are at a 2-4 leaf stage. For that purpose the various seed species are sown in time-staggered relationship. The greenhouse conditions (temperature, light) are as in Example 28. Determination of the herbicidal effect is also effected 28 days after application according to the method of Example 26.

Particular advantageous herbicidal properties are i.a. observed with the compounds of the Examples 4.3, 6, 7.2, 7.3, 7.4, 7.5 and 7.6. Some of the results obtained with application rates corresponding to 0.2 kg, 1 kg and 5 kg active ingredient/hectare have been summarised herein before. (See also Tables A and B hereinafter).

TABLE A

| | Compound of Example 6 - % damage | | | | | |
|---|---|---|---|---|---|---|
| | Pre-emergence | | | Post-emergence | | |
| Plant treated | kg/ha | | | | | |
| | 0.2 | 1.0 | 5.0 | 0.2 | 1.0 | 5.0 |
| *Amaran. retrofl.* | 80 | 100 | 100 | 90 | 100 | 100 |
| *Capsella b.p.* | 90 | 100 | 100 | 90 | 100 | 100 |
| *Chenop. alb.* | 100 | 100 | 100 | 100 | 100 | 100 |
| *Galium aparine* | 0 | 10 | 100 | 0 | 0 | 80 |
| *Senecio vulg.* | 30 | 100 | 100 | 70 | 100 | 100 |
| *Stellaria media* | 100 | 100 | 100 | 50 | 100 | 100 |
| Alfalfa | 90 | 100 | 100 | 30 | 100 | 100 |
| Bean | 10 | 100 | 100 | 30 | 70 | 100 |
| Carrot | 90 | 100 | 100 | 80 | 100 | 100 |
| Cotton | 0 | 0 | 30 | 10 | 30 | 100 |
| Flax | 50 | 100 | 100 | 20 | 100 | 100 |
| Potato | 0 | 70 | 100 | 0 | 10 | 90 |
| Soya | 0 | 10 | 100 | 0 | 10 | 100 |
| Sugar beet | 90 | 100 | 100 | 100 | 100 | 100 |
| Rape | 10 | 100 | 100 | 20 | 100 | 100 |
| Sunflower | 20 | 100 | 100 | 90 | 100 | 100 |
| *Agropyron repens* | 0 | 0 | 20 | 0 | 0 | 0 |
| *Agrostis alba* | 90 | 100 | 100 | 90 | 100 | 100 |
| *Alopec. myos.* | 30 | 100 | 100 | 30 | 100 | 100 |
| *Apera sp. venti.* | 80 | 100 | 100 | 60 | 100 | 100 |
| *Avena fatua* | 100 | 100 | 100 | 10 | 80 | 100 |
| *Echinochloa c.g.* | 50 | 100 | 100 | 0 | 90 | 100 |
| Corn | 0 | 80 | 80 | 0 | 0 | 70 |
| Wheat | 0 | 10 | 100 | 0 | 0 | 10 |

TABLE B

| | POST EMERGENCE APPLICATION | | | | | | | |
|---|---|---|---|---|---|---|---|---|
| | Compound I Tested - % damage | | | | | | | |
| | Ex. 7.4 | | Ex. 7.5 | | Ex. 7.6 | | Standard* | |
| Plant treated | kg/ha | | | | | | | |
| | 0.2 | 1.0 | 0.2 | 1.0 | 0.2 | 1.0 | 0.2 | 1.0 |
| *Amaran. retrofl.* | 80 | 100 | 100 | 100 | 100 | 100 | 0 | 70 |
| *Capsella b.p.* | 100 | 100 | 100 | 100 | 100 | 100 | 30 | 50 |
| *Chenop. alb.* | — | — | 100 | 100 | 100 | 100 | 80 | 100 |
| *Galium aparine* | 10 | 80 | 70 | 70 | 30 | 80 | 0 | 0 |
| *Senecio vulg.* | 90 | 100 | 80 | 100 | 100 | 100 | 90 | 100 |
| *Stellaria* | 60 | 100 | 60 | 100 | 100 | 100 | 80 | 100 |

TABLE B-continued

POST EMERGENCE APPLICATION

| Plant treated | Compound I Tested - % damage | | | | | | | |
|---|---|---|---|---|---|---|---|---|
| | Ex. 7.4 | | Ex. 7.5 | | Ex. 7.6 | | Standard* | |
| | 0.2 | 1.0 | 0.2 | 1.0 | 0.2 | 1.0 | 0.2 | 1.0 |
| | kg/ha | | | | | | | |
| *media* | | | | | | | | |
| Alfalfa | 100 | 100 | 50 | 100 | 30 | 100 | 20 | 20 |
| Bean | 90 | 100 | 10 | 100 | 40 | 100 | 10 | 20 |
| Carrot | 90 | 100 | 100 | 100 | 60 | 80 | 90 | 100 |
| Cotton | 100 | 100 | 50 | 100 | 70 | 100 | 10 | 20 |
| Flax | 100 | 100 | 30 | 100 | 100 | 100 | 30 | 60 |
| Potato | 10 | 10 | 20 | 10 | 10 | 30 | 0 | 0 |
| Soya | 40 | 100 | 10 | 10 | 20 | 30 | 10 | 0 |
| Sugar beet | 100 | 100 | 100 | 100 | 70 | 100 | 90 | 100 |
| Rape | 100 | 100 | 100 | 100 | 90 | 100 | 30 | 100 |
| Sunflower | 100 | 100 | 100 | 100 | 100 | 100 | 70 | 100 |
| *Agropyron repens* | 0 | 0 | 0 | 0 | 0 | 0 | 0 | 0 |
| *Cyperus rotundus* | 0 | 0 | 0 | 0 | 20 | 20 | 0 | 0 |
| *Alopec. myos.* | 20 | 100 | 0 | 70 | 0 | 100 | 10 | 40 |
| *Apera* sp. *venti.* | 80 | 100 | 100 | 100 | 30 | 100 | 40 | 100 |
| *Avena fatua* | 60 | 100 | 10 | 20 | 0 | 20 | 20 | 50 |
| *Echinochloa c.g.* | 10 | 100 | 0 | 90 | 30 | 50 | 0 | 90 |
| *Echinochloa c.g.* (paddy cond.) | 90 | 100 | 20 | 100 | 100 | 100 | 10 | 100 |
| Corn | 10 | 30 | 0 | 0 | 0 | 0 | 10 | 20 |
| Wheat | 0 | 10 | 0 | 0 | 0 | 0 | 0 | 10 |
| Rice (paddy) | 20 | 100 | 0 | 100 | 70 | 80 | 0 | 0 |

Standard*: N'—[4-(1-methylethyl)phenyl]-N,N—dimethylurea

What we claim is:

1. The compound of the formula:

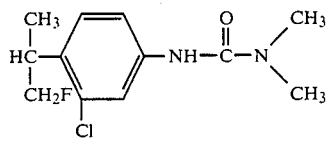

2. A method of combatting weeds in a locus, which comprises applying to the locus thereof the herbicidally effective amount of a compound of claim 1.

3. A method of combatting weeds in a crop locus which comprises applying to said locus a selective herbicidally effective amount of the compound of claim 1.

4. The method of claim 3 in which the compound is applied pre-emergent.

5. The method of claim 3 in which the compound is applied post-emergent.

6. The method of claim 4 in which the compound is applied pre-emergent and in which the crop is wheat, corn, soybean or potato.

7. The method of claim 5 in which the compound is applied post-emergent and in which the crop is wheat, corn, soybean or potato.

8. The method of claim 6 in which the crop is wheat.

9. The method of claim 6 in which the crop is corn.

10. The method of claim 7 in which the crop is wheat.

11. The method of claim 7 in which the crop is corn.

12. A herbicidal composition comprising a herbicidally acceptable diluent and a herbicidally effective amount of the compound of claim 1.

* * * * *